United States Patent [19]

Yabe

[11] Patent Number: 4,885,634
[45] Date of Patent: Dec. 5, 1989

[54] ENDOSCOPE APPARATUS CAPABLE OF MONOCHROME DISPLAY WITH RESPECT TO SPECIFIC WAVELENGTH REGIONS IN THE VISIBLE REGION

[75] Inventor: Hisao Yabe, Hachioji, Japan

[73] Assignee: Olympus Optical Co., Ltd., Tokyo, Japan

[21] Appl. No.: 226,486

[22] Filed: Aug. 1, 1988

[30] Foreign Application Priority Data

Oct. 27, 1987 [JP] Japan .................................. 62-272611

[51] Int. Cl.[4] .......................... A61B 1/04; H04N 7/18
[52] U.S. Cl. ....................................... 358/98; 358/27; 128/6
[58] Field of Search .................. 358/98, 28, 93, 1, 29, 358/21 R, 185; 128/4, 6

[56] References Cited

U.S. PATENT DOCUMENTS 4,799,104 1/1989 Hosoya et al. .......................... 358/98
4,807,026 2/1989 Nishioka et al. ....................... 358/98

Primary Examiner—Howard W. Britton
Assistant Examiner—Victor R. Kostak
Attorney, Agent, or Firm—Armstrong, Nikaido, Marmelstein, Kubovcik & Murray

[57] ABSTRACT

An endoscope apparatus equipped with a device for generating color image signals for a normal color display from image signals picked up by using a solid image pickup element under an illuminating device covering the visible light region, and output terminals adapted to output those image signals which are exclusively based on specific wavelength components, the endoscope apparatus allowing a monochrome image with respect to a specific wavelength region to be displayed along with a normal color image.

26 Claims, 8 Drawing Sheets

FIG. 11
| Mg | G1 | Mg | G1 |
| Cy1 | Ye | Cy1 | Ye |
| Bl | G2 | Bl | G2 |
| Cy2 | R | Cy2 | R |
FIG. 12A
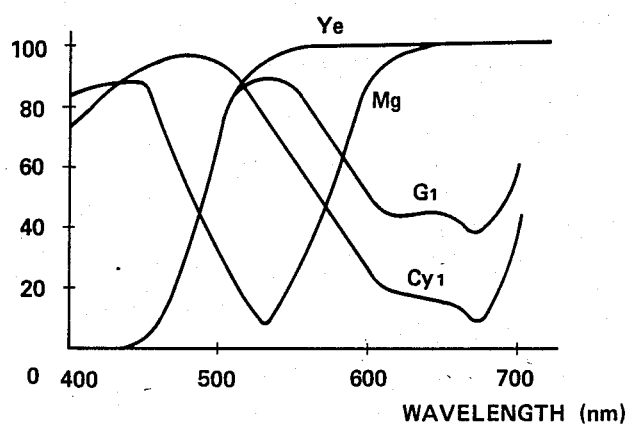
FIG. 12B
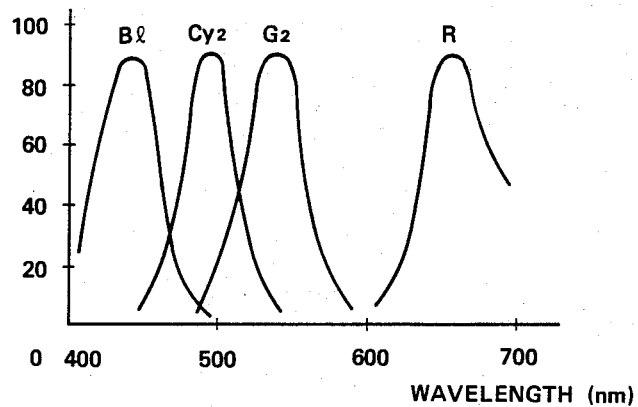

ENDOSCOPE APPARATUS CAPABLE OF MONOCHROME DISPLAY WITH RESPECT TO SPECIFIC WAVELENGTH REGIONS IN THE VISIBLE REGION

BACKGROUND OF THE INVENTION

Field of the Invention and Description of the Related Art

This invention relates to an endoscope apparatus which is equipped with a signal processing means enabling monochrome images with respect to specific wavelength components to be diplayed as well as color images by visible light, so that the diagnostic functions thereof may be substantially improved.

Recently, television cameras using a solid image pickup elements such as CDD as the image pickup means are being widely used. Such image pickup means have also come to be used in endoscopes.

Conventionally, a visible light image (ca. 400 to 700 nm) is picked up by means of said CDD or the like and is transformed into a video signal, to be color-displayed on an observation monitor. As a result, what can be obtained are the same images that one can see with the naked eyes while using a fiber scope. As to the diagnostic functions of an endoscope using such image pickup means, they are not very much different from those of a fiber scope.

In view of this, a picture processing or a picture analysis has been performed on the image signals of the endoscope, from which the following have become apparent:

(a) The inner celom walls have colors of various shades of red. However, it is appreciated, by depicting them with the red component alone, that they contain few high-frequency components (fine variations on the subject present no great contrast) and give a flat or hazy impression, thereby detriorating the contrast for the entire visible wavelength region.

(b) On the other hand, the red component excels in mucosal permeability and is more useful in depicting sub-mucosal blood vessels than the green and blue components. In other words, when observing sub-mucosal vessels, the green and blue components deteriorate the contrast in the images.

(c) The green component, to which the human eyes are highly sensitive, is the main contrast factor in an endoscope. Further, it conveys more information than the blue component (the inner celom walls present intrinsically little blueness, and solid image pickup elements have generally poor sensitivity to blue), so that they can provide images with a satisfactory S/N. Since the blue component has a short wavelength, it is reflected at positions which are quite near to the surfaces of the inner celom walls. Accordingly, it is useful in depicting fine surface irregularities.

However, it would render the image quite uncomfortable to watch to display exclusively the red component as red, the green component as green, and the blue component as blue. An appropriate light intensity adjustment could not then be effected, either,

SUMMARY OF THE INVENTION

Accordingly, it is an object of the present invention to provide an endoscope apparatus making it possible to obtain endoscopic images which have highly effective diagnostic functions.

Another object of this invention is to provide an endoscope apparatus which is equipped with an ordinary color display function so that it can be used in a variety of ways.

In accordance with this invention, there are provided a means for picking up the image of a subject illuminated by a illuminating means covering the visible region in order to color-dislplay it in an ordinary manner, and a signal processing means and a display means thereof for processing signals with respect to specific wavelength components such as red, green and blue and for displaying them, thereby making it possible to display the inherent pieces of image information obtained by different wavelength components in such a manner that they can be easily discriminated from each other.

More specifically, since the red component enables the running condition of sub-mucosal or sub-epithelial blood vessels to be observed more clearly, any sub-mucosal or sub-epithelial degeneration due to some disease can be recognized together with the nature thereof.

In the diagnosis of microcancers, generation of a micro-reddening (which is perceived as change in brightness), reddening pattern (which is perceived as change in color, and in particular, change in brightness) and fine surface irregularities are the diagnostic indexes, of which the change in brightness is more clearly shown by the green component and the surface irregularities by the blue component.

BRIEF DESCRIPTION OF THE DRAWINGS

FIG. 11 is a schematic view showing the filter arrangement in the mosaic color filter;

FIGS. 12A and 12B are characteristic diagrams showing the spectral transmission characteristics of the filters shown in FIG. 11;

DETAILED DESCRIPTION OF THE PREFERRED EMBODIMENTS

Figure 1:
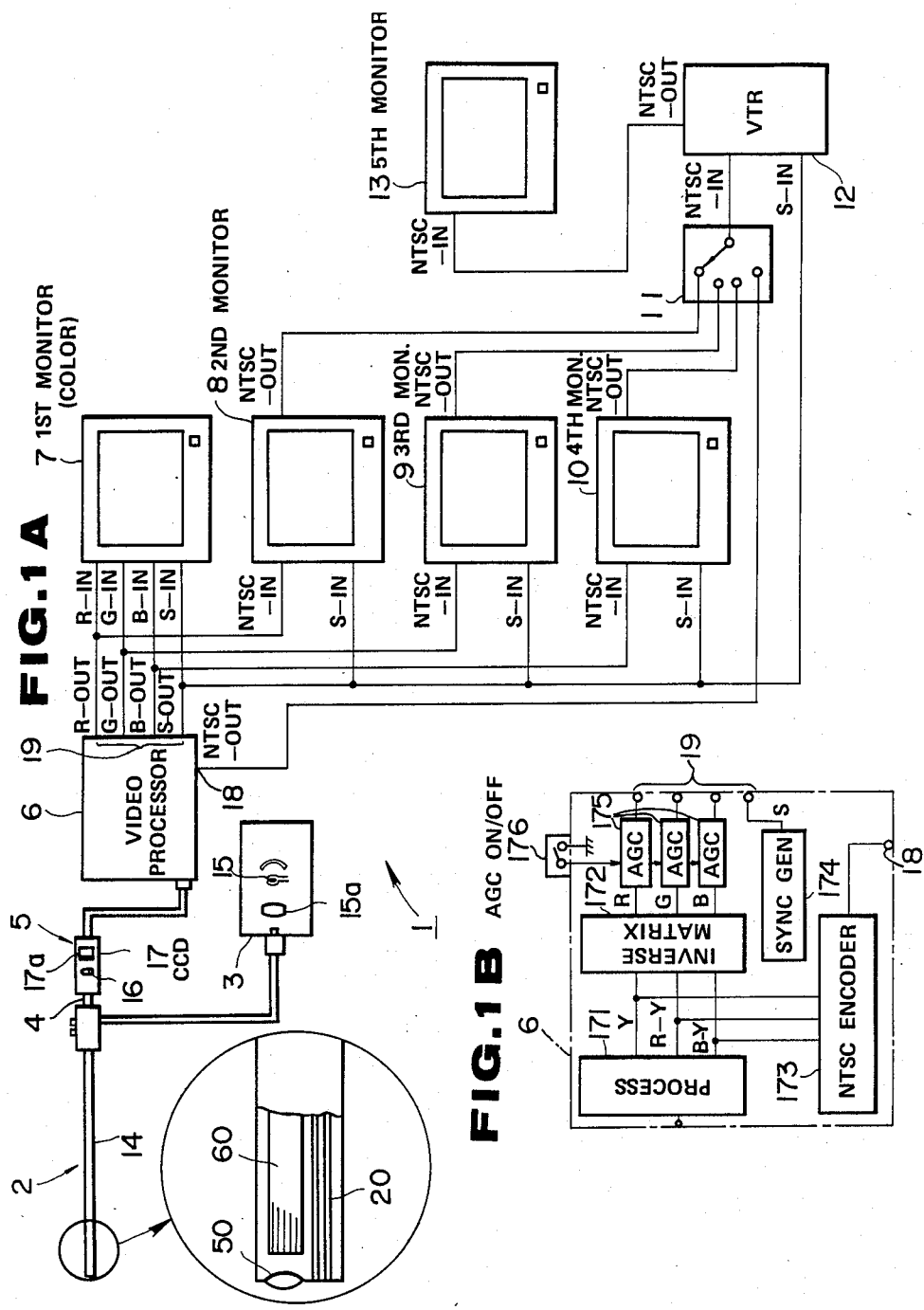
FIG. 1A is a block diagram showing the configuration of the first embodiment of an endoscope apparatus in accordance with this invention.
FIG. 1B is a block diagram showing the configuration of the video processor in the first embodiment.

As shown in FIG. 1A, an endoscope apparatus 1 in accordance with the first embodiment comprises a fiber scope 2, a light source apparatus 3 adapted to supply illuninating light to this fiber scope 2, a camera head 5 attached to an eyepiece section 4 of the fiber scope 2, a video processor 6 having a signal processing means for this camera head 5, a plurality of observation monitors 7, 8, 9, 10 (first to fourth ones) adapted to display image signals output by this video processor 6, a VTR 12 connected to these monitors 7, 8, 9, 10 through the intermediary of a video switcher 11, and a fifth observation monitor 13 connected to the output terminal of this VTR 12.

The above-mentioned fiber scope 2 has an elongate inserting section 14, into which a light guide 20 is inserted. This light guide 20 is passed through a light guide cable extending from an operation section, and white light is supplied from the light source apparatus 3. In other words, the white light from a lamp 15 is condensed by means of a condenser lens 15a and applied to the incidence end surface of the light guide 20. The image of the subject illuminated by this light guide 20 is formed by means of an objective 50 mounted on the front end portion of the inserting section 14 and is transmitted to the side of the eyepiece section 4 by means of an image guide 60 with an incidence end surface arranged on the focal surface thereof. Then, the image is formed on a CCD 17 by means of an image formation lens 16 in the camera head 5 which is detachably set with respect to the eyepiece portion 4. The camera head 5 is a single-plate-type color image pickup means which consists of a mosaic filter 17a in which color transmission filters of, for example, R, G, B are arranged. This mosaic filter 17a is attached to the image pickup surface of the CCD 17. (A three-plate-type or a three-tube-type image pickup means may naturally be adopted.)

The CCD 17 of this camera head 5 reads out the picked-up signal charge by the drive signal of a drive circuit (not shown) in the video processor 6 and outputs an NTSC composite video signal from an NTSC output terminal 18 by means of an image signal processing means in this video processor 6. At the same time, it outputs RGB video signals through RGB output terminals 19 of the NTSC system.

Said video processor 6 generates, as shown in FIG. 1B, a luminance signal Y and pigment signals R-Y, B-Y by a processing circuit 171, and three primary color signals R, G and B by an inverse matrix circuit 172 as well as NTSC composite video signals through an NTSC encoder 173. A synchronizing signal generator 174 generates synchronizing signals. The signals from the above inverse matrix circuit 172 are output at RGB output terminals 19 through respective AGC circuits 175. The AGC circuits 175 are capable of ON/OFF switching of AGC by means of an AGC ON/OFF switch 176.

Said RGB output terminals 19 are composed of four output terminals, i.e., a Red signal output terminal (represented as R-OUT in FIG. 1), a Green signal output terminal (represented as G-OUT in FIG. 1), a Blue signal output terminal (represented as B-OUT in FIG. 1), and a Synchro signal output terminal (represented as S-OUT in FIG. 1).

A monitor 7 is connected to the four output terminals 19 of said video processor 6, and monitors 8, 9 and 10 are connected to the terminals R, G, B and S. A monitor 13 is connected to the VTR 12. These monitors are all capable of external synchronization, each performing a display synchronized with the synchronization signal output from the terminal S. Further, at least the first monitor 7 and the fifth monitor 13 are color monitors. On the other hand, the second, third, and fourth monitors 8, 9 and 10 may be monochrome or color monitors.

The first monitor 7 is an NTSC-RGB type observation monitor having RBG video signal input terminals of the NTSC type.

On the other hand, the second, third and fourth monitors 8, 9 and 10 are NTSC type composite type monitors each having an NTSC composite video signal input terminal (NTSC-IN), an NTSC-Synchro signal input terminal (S-IN) and an NTSC composite video signal output terminal (NTSC-OUT). They are externally synchronized by the Synchro signal and display the contents of video signals from the NTSC-IN. Further, they output video signals from the NTSC-IN through the NTSC-OUT.

The fifth monitor 13 is an NTSC composite type monitor. The VTR 12 is a NTSC composite type VTR having an NTSC composite video signal input terminal (NTSC-IN), an Synchro signal input terminal (S-IN) and an NTSC composite video signal output terminal (NTSC-OUT) and performs recording and reproduction of images. Here, the recording and reproduction signals include a synchronizing signal.

On the first monitor 7 are color-displayed with a predetermined color reproducibility an endoscopic image of a wavelength region (generally equal to the entire visible region) which is determined by, for example, the spectral intensity of the lamp 15 in the light source apparatus 3, the spectral transmission characteristics of the light guide and image guide of the fiber scope 2, the spectral sensitivity of the image pickup means of the camera head 5, i.e., the CCD 17, the color filter characteristics of the mosaic color filter 17a, the color characteristics of the signal processing system of the video processor 6, and the color characteristics of the first monitor 7.

On the above second, third and fourth monitors 8, 9 and 10 are respectively monochrome-displayed the red, green and blue components of an endoscopic image.

Here, the wavelength regions and the spectral characteristics of the red, green and blue components are determined by the above-described characteristics. In particular, when the color image pickup means of the camera head 5 is a single-plate camera and the signal Y (luminance signal) and the signals R-Y, B-Y are to be output, the wavelength region is mainly determined by such factors as the matrix of the inverse matrix circuit 172 (which is in the video processor 6) for preparing the NTSC-RGB video signal from these signals and the spectral transmission characteristics of the color filter.

The brightness of the images displayed on the second, third and fourth monitors 8, 9 and 10 may not be properly adjusted depending on the subject. Since the inner celom walls are generally tinged with a reddish color, the second monitor 8 generally tends to be over-illuminated, whereas the fourth monitor 10 tends to be under-illuminated. Accordingly, brightness correction may be effected using the brightness adjusting mechanism with which each of the second, third and fourth monitors 8, 9 and 10 are equipped. The correction may also be effected by turning on the AGC ON/OFF switch. As for the output from the VTR 12, such a correction can be performed each time using the brightness adjusting mecanism with which the fifth monitor 13 is equipped.

By inputting NTSC composite video signals from the video processor 6 to the NTSC composite type monitor and displaying the same with reduced chroma (saturation), a monochrome image can be obtained. The wavelength region 0.30R+0.59G+0.11B of this image covers the entire wavelength region components, so that when compared with the monochrome display using each of the wavelength regions exclusively, the diagnostic merits inherent to each of the wavelength regions are impeded (i.e., greater diagnositc merits can be provided by exclusively using one of the wavelength components).

The VTR 12 is capable of recording the color composite signals selected by the switcher 11 or recording ordinary NTSC composite (color) video signals, so that it can display these selected color signals on the monitor 13, in addition to the color-display in an ordinary manner.

In accordance with this first embodiment, a selective monochrome display can be effected by means of the color signal of each of the various wavelength regions alone, so that different features can be made conspicuous with respect to the same region of interest, thus improving the diagnositic efficiency.

Figure 2:
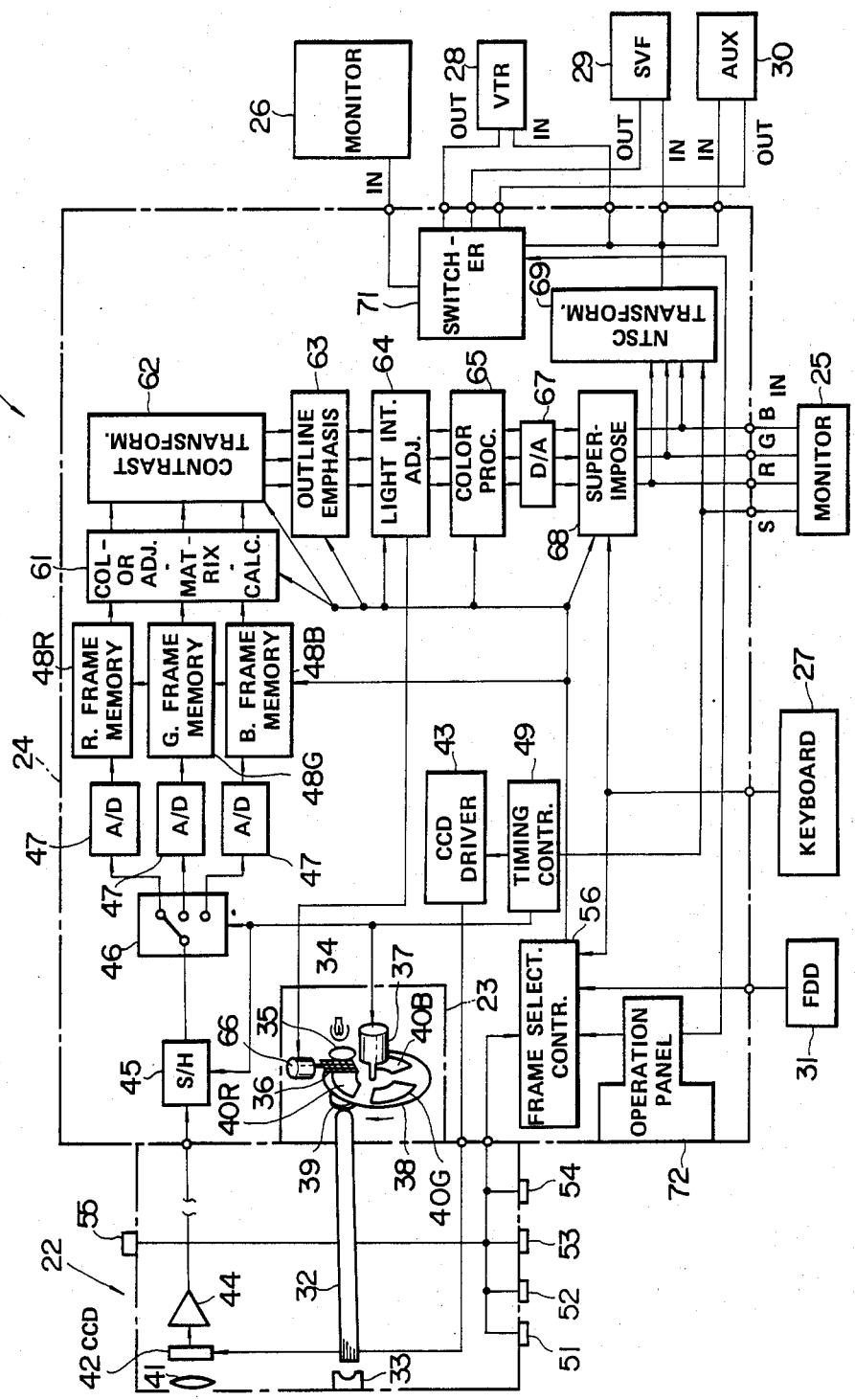
FIG. 2 is a block diagram showing the configuration of the second embodiment of an endoscope apparatus in accordance with this invention.

FIG. 2 shows the second embodiment of an endoscope apparatus 21 in accordance with this invention.

This endoscope 21, which is the second embodiment of this invention, comprises: an electronic scope 22; an endoscope controller (video processor) 24 having a built-in surface-sequential-type light source section 23 as well as a built-in signal processing means for said electronic scope 22; an NTSC-RGB type monitor 25 and an NTSC-composite video type monitor 26 for displaying the video signals processed by said video processor 24; a keyboard 27 for performing various signal processing operations; a VTR 28, a still video floppy apparatus (SVF) 29 for picking up images, and other recording devices (AUX) 30 for recording/reproducing the composite video signals input to said monitor 26; and a floppy disk drive apparatus (FDD) 31.

A light guide 32 is inserted into said electronic scope 22, and illuminating light supplied by light source section 23 to the incidence end surface is transmitted through this light guide, to be applied to the subject through an outgoing end surface and an illuminating lens 33. This light source section 23 serves to form a parallel beam out of the light from an illuminating lamp 34 by means of a collimating lens 35. The beam is then passed through a diaphragm 36 and a rotary filter 38 rotated by means of a motor 37, providing illuminating lights of the wavelength regions of red, green and blue. Then, it is applied to the incidence end surface of the light guide 32 after being condensed by a condenser lens 39.

A fan-shaped red-transmission filter 40R, green-transmission filter 40G and a blue-transmission filter 40B are mounted on said rotary filter 38, and by rotating the rotary filter 38, the transmission filters 40R, 40G and 40B are successively placed in the path of the beam. Accordingly, the illuminating lights of red, green and blue are sequentially applied to the incidence end surface of the light guide 32, and the subject is also successively illuminated by the illuminating lights of red, green and blue.

The image of the subject thus illuminated by the illuminating light transmitted by said light guide 32 is formed on the image-pickup surface of a CCD 42 by means of an objective 41 mounted on the front end portion of the electronic scope 22.

This CCD 42 effects photoelectric conversion of an optical image and stores it as a signal charge, which is read out by applying a drive signal from a CCD drive 43 in the video processor 24 and amplified by a preamplifier 44. Then, it is conveyed through a signal cable and input to a sample hold circuit 45 in the video processor 24 for sample holding. The signal which has thus undergone sample holding is transformed into a digital signal by an A/D converter 47 through a multiplexer 46. Then, it is written to an R frame memory 48R, a G frame memory 48G and a B frame memory 48B.

The sampling pulses of the above sample hold circuit 45 are generated in synchronization with a timing signal from a timing control circuit 49. The multiplexer 46 is controlled in synchronization with the timing signal of the timing circuit 49.

For example, upon termination of the period during which the color transmission filters 40R, 40G and 40B in the above light source section 23 are placed in the light path, i.e., upon termination of the illumination period of the red, green and blue, the timing control circuit 49 applies a timing signal for outputting drive signals, to the CCD drive 43. At the same time, it effects switching of the multiplexer 46 (the switching of this multiplexer 46 may also be effected before the termination period expires).

The red-transmission filter 40R (hereinafter referred to as "R-filter", which also applies to the other transmission filters 40G and 40B) has its peak at ca. 600 nm and transmits light beams in a wavelength range of ca. 535 to ca. 700 nm. The G-filter 40G has its peak at ca. 535 and transmits light beams in a wavelength range of ca. 470 nm to ca. 605 nm. The B-filter 40B has its peak at ca. 450 nm and transmits light beams in a wavelength range of ca. 390 nm to ca. 520 nm. Thus, the wavelength ranges of the R-, G- and B-filters 40R, 40G and 40B overlap each other so that the color reproducbility for the normal color observation may be improved. Although this embodiment is sufficiently effective with this arrangement, it is more desirable to avoid such an overlap. Accordingly, it may be so arranged that the rotary filter 38 can be used with non-overlapping R-, G-, B-filters.

While the color image pickup method in this embodiment is of the surface sequential type, it is desirable, in the case of an electronic scope with built-in color filters for image pickup under white illumination, to avoid overlapping of the trasmission wavelength regions of the color filters attached to the CCD. However, if they overlap each other, it is possible to exclusively output specific wavelength region components by an image processing operation which is to be described later.

The lens 35 and the condenser lens 39 for forming a parallel beam out of the light from the above-mentioned illuminating lamp 34 as well as the light guide lens 32, the illuminating lens 33 and objective 41 allow the lights of the entire visible region to be transmitted, and the CCD 42 is sensitive at least to lights of ca. 390 to 700 nm.

The above-mentioned electronic scope 22 includes first, second, third, fourth and fifth switches 51, 52, 53, 54 and 55 provided in the operation section, which switches are connected to a frame selection control circuit 56 in the video processor 24.

In the above R, G and B frame memories 48R, 48G and 48B, image signals picked up under illumination lights of red, green and blue are read out as soon as they are written to them, one frame at a time, and input to a color adjustment/matrix/calculation circuit 61, and after color adjustment by the gain variation of the color signal, the matrix transformation and the various calculations, they are input to a contrast transformation circuit 62 to undergo contrast transformation. After that, they are input to an outline emphasis circuit 63 to effect outline emphasis, and input to a light intensity adjustment circuit 64. The signals input to this color intensity adjustment circuit 64 are output to a color processing circuit 65 in the next step. At the same time, light intensisty adjustment control signals are generated and applied to a diaphragm controller 66 of the diaphragm 36 so as to control the aperture of the diaphragm 36. This diaphragm controller 66 is composed of the diaphragm 36, a motor for rotating this diaphragm 36, and a motor drive not shown.

After the color processing in the above color processing circuit 65, they are converted into analog signals by means of a D/A converter 67. Then, they are input to a superimpose circuit 68, where character signals or the like input through the keyboard 27 are superimposed. After that, they are output to the monitor 25 through the RGB output terminals as well as to an NTSC transformation circuit 69. The composite video signals of this NTSC transformation circuit 69 are input through the NTSC composite video output terminals to the VTR 28, the SVF 29, the AUX 30 and a switcher 71. The output terminals of the VTR 28, the SVF 29 and the AUX 30 are connected to the switcher 71, any of these selected being displayed on the monitor 26.

An operation panel 72 is provided in the front face of the video processor 24. The manipulation of the switches etc. on this panel 72 is transmitted to the frame selection control circuit 56. At the same time, the manipulation of these switches etc. enables the selection of the switcher 71 to be controlled.

Figure 3:
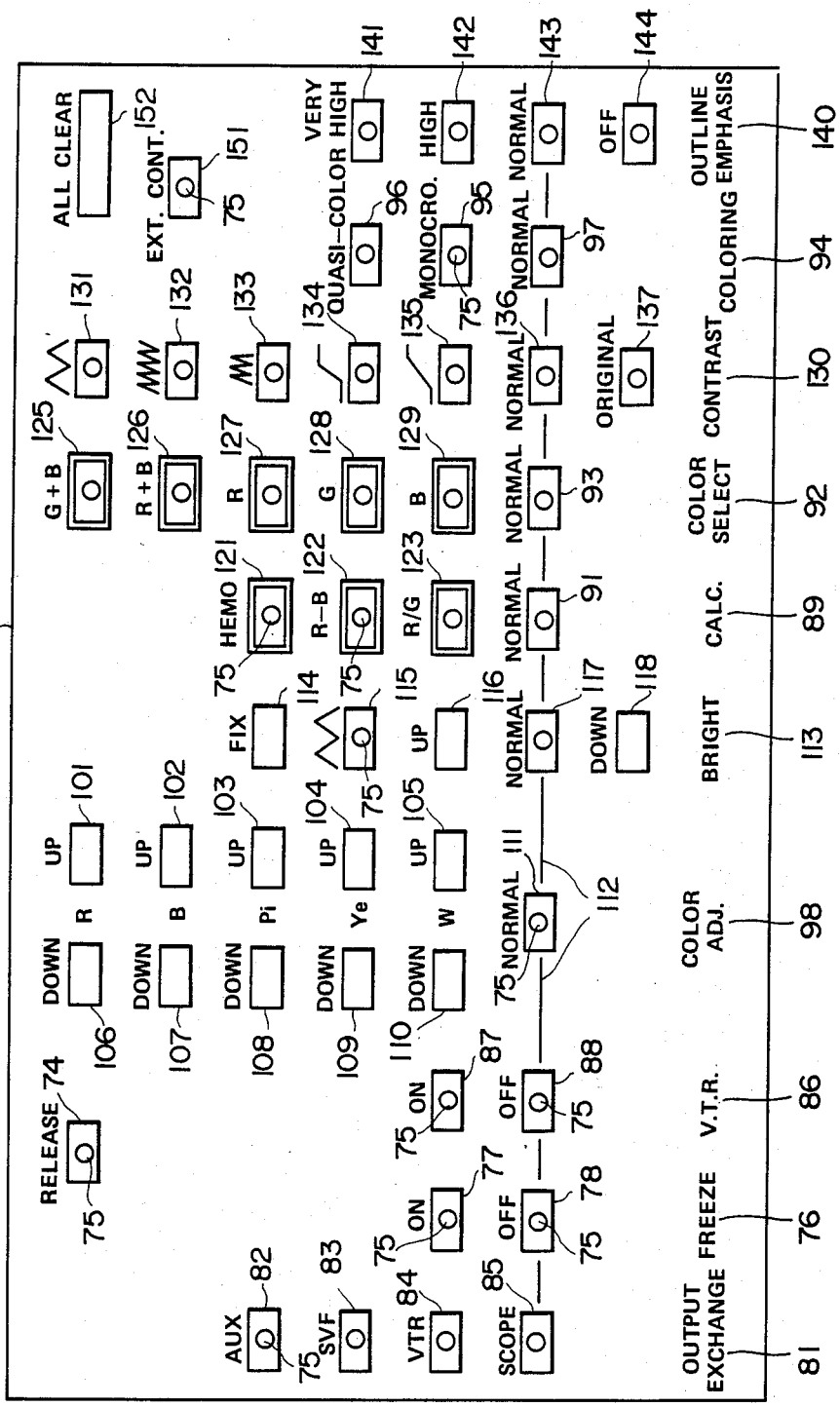
FIG. 3 is a front view illustrating the switches provided on the operation panel.

The first switch 51 provided in the operation section of the above electronic scope 22 is a release switch having the following release functions:

By pressing the first switch 51, a release trigger signal is imparted to the SVF 29 and the AUX 30. This release trigger signal can also be generated by means of a release switch 74 provided on the operation panel 72 shown in FIG. 3.

This release switch 74 is equipped with an LED 75 indicated by a circle. Of the rectangular switches shown in FIG. 3, those which have no circles are push-button switches with no LED and those marked with circles are self-illuminating type push-button switches equipped with LED.

Accordingly, by pressing the first switch 51 or the release switch 74, release is effected upon the command from the frame selection control circuit 56. At this time, the LED 75 of the release switch 74 is ON for 0.5 second, and then goes out automatically (Normally, this LED is OFF), thus notifying that release has been effected.

The freeze function will now be explained.

The second switch 52 is a freeze switch. By pressing this switch, freeze is effected. Another pressing of this switch releases the freeze. This freeze is effected by stopping the writing with respect to the frame memories 48R, 48G and 48B through the frame selection control circuit 56, so that the functions of the circuits in the after steps (i.e, the color adjustment/matrix/calculation circuit 61, the contrast transformation circuit 62, the outline emphasis circuit 63, the color processing circuit 65, the superimpose circuit 68, etc.) are in operation during the freeze.

Further, freeze is effected by pressing the freeze switch 77 of the freeze switch group 76 on the operation panel 72. By pressing the freeze releasing switch 78, the freeze is released. During the freeze, the LED 75 of the freeze switch 77 is ON. Normally, the LED 75 of the freeze releasing switch 78 is ON.

Next, the output exchange function will be explained.

One output switch is to be selected out of the four output switches composing the output exchange switch group 81 on the operation panel 72, i.e., an AUX output switch 82, an SVF output switch 83, a VTR output switch 84 and a SCOPE output switch 85. They control the video switcher 72 according to the results and select the NTSC composite video signal of the AUX 30 o the SVF 29 or the VTR 28 or the NTSC transformation circuit 69, which they output to the monitor 26. Here, the LED 75 of the switch selected from the switches 81, 82, 83, 84 or 85 comes on, those of the other switches going out.

Next, the VTR control function will be explained.

When the VTR 28 is in the REC PAUSE condition, pressing of a VTR ON switch 87 composing a VTR ON/OFF switch group 86 results in the REC PLAY condition, the LED 75 of this switch coming on. On the other hand, by pressing a VTR OFF switch 88 results in the REC PAUSE condition, the LED 75 of this swich 88 going out.

When, on the other hand, the VTR 28 is in the PAUSE condition, pressing of the VTR ON switch 87 results in the PLAY condition, the LED 75 of this switch 87 coming on. The pressing of the VTR OFF switch 88 results in the PAUSE condition, the LED 75 of this switch 88 coming on.

Next, the color adjustment function will be explained.

The color adjustment function is only then in operation when a normal output switch 91 is set (selected) out of a calculation switch group 89 and a normal output switch 93 out of a color selection switch group 92. Otherwise, it is in the reference gain condition.

In this reference gain condition, the entire visible light region is color-displayed in a normal manner. In the case of a coloring switch group 94, the gains of the R, G and B are restored to the reference condition when a monochrome display switch 95 is set. In other words, the color adjustment function does not work. When a quasi-color switch 96 is selected out of the coloring switch group 94, this switch group 94 operates in the same manner as in the case of a normal image switch 97.

A color adjustment switch group 98 is provided on the above operation panel 72. This switch group 98 consits of gain increasing switches 101, 102, 103, 104 and 105 for red, blue, pink, yellow and white which are arranged on the right-hand side of the letters R, G, Pi, Ye and W, respectively, as well as gain decreasing switches 106, 107, 108, 109 and 110 which arearranged on the left-hand side thereof. The color adjustment/matrix/calculation circuit 61 effects intermittent change in color in accordance with the operation of these switches 101 to 110. For example, when the switch 101 is pressed once, the R-gain is increased by 1 step, resulting in a color 1 step more reddish. Another pressing of the switch results in a color still 1 step more reddish. The change in color is not accompanied by change in brightness since the light intensity adjustment by the light intensity adjustment circuit 64 is performed on the basis of the output signals from the color adjustment-/matrix/calculation circuit 61.

By pressing the switch 103, for example, a color 1 step more pinkish is obtained, and by pressing the switch 104, a color 1 step more yellowish. Prssing of the switch 105 results in a color 1 step more whitish. (The saturation is lowered.) Since the light intensity adjustment circuit 64 is provided in the after step, the brightness is constant for every case.

Now, it is a physician and not a specialist in color adjustment that performs endoscopic examinations. Accordingly, it is easier to directly obtain a pinkish, yellowish, or whitish color, for example, than performing color adjustment by controlling the amount of the red and blue. Here, the expression "whitish" does not imply brightness but the degree of saturation. As for the brightness, it can be adjusted separately. Further, a more greenish, more orangy, or more pallid color may be obtained in the same manner. Particularly important are pink, yellow and white.

From the structural viewpoint, the R, G and B gains are controlled by a well-known method.

By pressing a reference color switch 111 of said color adjustment switch group 98, a reference gain is applied to each of the R, G, B components, which results in a reference color balance, the LED 75 of this switch 111 coming on. The electronic scope 22 has the merit of enabling various picture processings and picture analyses to be performed. Accordingly, it is desirable that raw data which has been processed as little as possible can be output. In view of this, it is so arranged that it can perform reference output operation. The image processing apparatus etc. can be connected to the NTSC-RGB output terminals in place of the monitor 25.

The magnification of the gains imparted to the RGB colors with respect to the reference gain is displayed in a superimposed condition.

The lines extending on the both sides of the reference color switch 111 represent normal lines 112.

The light intensity adjustment function will now be explained.

The light intensity adjustment circuit 64 serves to control the aperture of the diaphragm 36 in such a manner that the magnitude of the image signal input to this circuit 64 is adjusted to a preset value. The preset value is changed stepwise or gradually by operating a brightness switch group 113. This brightness switch group 113 includes a brightness fixing switch 114, a brightness varying switch 115, a brightness increasing switch 116 a brightness normalizing switch 117 and a brightness decreasing switch 118.

By pressing the brightness increasing switch 116 once, the preset value is increased by 1 step, the endoscopic images on the monitors 25 and 26 becoming 1 step brighter. Another pressing of this switch 116 results in a brightness which is still increased by 1 step. When, on the other hand, the brightness decreasing switch 118 is pressed, the brightness is decreased by 1 step.

By pressing the brightness varying switch 115, the LED of this switch 115 comes on. At the same time, the diaphragm controller 66 drives, in accordance with the command from the light intensity adjustment circuit 64, the diaphragm 36 in such a manner that it reciprocates between the fully open and fully closed positions. As a result, change in brightness is repeated between the bright and dark states. Such a repeated change in brightness also occurs when the third switch 53 of the electronic scope 22 is pressed once, the LED 75 of the brightness varying switch 115 coming on.

When the above brightness varying switch 115 is ON, pressing of the brightness fixing switch 114 or the third switch 53 results in the brightness being fixed to the state. In other words, the magnitude of the image signal input to the light intensity adjustment circuit 64 reaches the set value, and after that an automatic light intensity adjustment is conducted in such a manner that the image signal attains that set value. At this time, the LED 75 of the brightness varying switch 115 goes out.

In the case of the contrast emaphasis which is to be described later, the appropriate range of brightness is narrower, so that the appropriate brightness can be easily obtained in this way, by means of the brightness varying function. When performing monochrome display after the color selection, it can also be utilized for changing brightness according to the case.

Since the light intensity adjustment circuit 64 is situated after the color adjustment/matrix/calculation circuit 61, the contrast transformation circuit 62 and the outline emphasis circuit 63, an automatic adjustment of light intensity can be performed based on the signals processed by these circuits 61, 62 and 63, so that an appropriate brightness can alway be attained. Further, the third switch 53 which is provided as the light intensity adjustment switch in the above electronic scope 22 serves to enhance its operability.

By pressing, on the other hand, the brightness normalizing switch 117, the light intensity level (set value) is set to the normal value. The LED 75 of this switch 117 comes on when the light intensity level is normal; otherwise, it goes out. The brightness variation may preferably be performed ca. 4 seconds per reciprocation. The variation will then be neither too fast nor too slow.

Next, the calculation functions will be explained.

Available as the calculation functions are a blood flow analysis mode as the first calculation mode, an R-B mode as the second calculation mode and an R/G mode as the third mode.

The caluculation switch group 89 includes a blood flow analysis switch 121 and an R-B output switch 122, an R/G output switch 123, and a normal output switch 91.

When the blood flow analysis switch 121 are pressed, the fourth switch 54, i.e., the multi-switch, is set to the blood flow function analysis mode, the LED 75 of this blood flow analyis switch 121 coming on. When in this condition the fourth swtich 54 is pressed, the LED of the blood flow analysis switch 121 comes on and the following calculation is performed in the color adjustment/matrix/calculation circuit 61: the calculation is conducted on the basis of the R-input from the picture elements i of the CCD 42 (this is represented by Rii. In other words, the Rii is the R-input of the i-th picture element into the color adjustment/matrix/calculation circuit 61) and the G-input (Gii) to generate the output Yoi of this circuit 61. (Here, the Yoi represents the luminance signal conversion output of the NTSC composite signal from this circuit 61 of the i-th picture element). Here, the output Yoi is expressed as:

$$Y_{oi} = C_1 \log_2\{(R_{ii} + C_2)/(G_{ii} + C_2)\}$$

where $C_1$ and $C_2$ are constants. By appropriately setting $C_2$ in accordance with the spectral transmission characteristics of the R, G, B filters 40R, 40G, 40B of the rotary filter 38, the spectral sensitivity characteristics of the CCD 42, the output characteristics of the video processor 24, etc., Yoi (the luminance signal level of each point) can have a positive correlation with the mucosal hemoglobin estimation (this is partly described in the "Examination of the picture analysis of gastric mucosal functions" in GASTROENTEROLOGICAL ENDOSCOPY, a journal issued by the Japanese Gastro-Endoscopy Society, Vol. 29, No. 3).

For example, the above constant $C_2$ is 1, and the values $C_1$ and $C_2$ can be set or changed at the keyboard 27. Here, when the coloring switch group 94 is set to a monochrome display switch 95 or a normal image switch 97 and the blood flow analysis mode is in operation, the LED 75 of the monochrome display switch 95 comes on.

By pressing the fourth switch 54 again, the image is restored to the normal (color) one when the coloring switch group 94 is set to the normal image switch 97. When the coloring switch group 94 is set to the monochrome display switch 95, the image is restored to the normal (monochrome) one.

When the coloring switch group 94 is set to a quasi-color switch 96, a quasi-color processing in accordance with the Y-signal is performed when the blood flow analysis mode is in operation, and when the operation stops, a normal image is normally color-displayed.

The fourth switch 54 arranged in the operation section of said electronic scope 22 provides a satisfactory operability, enabling an alternate comparison of the normal image with the calculation image. The blood flow analysis function can be jointly utilized with the outline emphasis function and the quasi-color function. It is also possible to effect switching of the light intensity adjustment as well as of the light intensity adjustment level.

While this mode is in operation, the gain with respect to the R, G, B signals is automatically set to the normal value (the LED 75 of a reference color switch 111 comes on), and is restored to the condition before the operation by stopping the operation. This mode has no influence on the set value of the light intensity adjustment level. The $C_1$ is set in such a manner that the normal brightness is obtained when the aperture of the diaphragm 36 is normal. However, this setting can be changed at the keyboard 27.

This calculation is perfomred on a digital basis. If the calculation takes too much time, the number of display frames may be reduced, for example, from 30 frames per sec. to 10 frames per sec., allowing the same contents to be output 3 frames at a time.

It will be supposed here that the R, G, B outputs from the color adjustment/matrix/calculation circuit 61 are: Roi=0.3Yoi, Goi=0.59Yoi, Boi=0.11 Yoi. (Roi is the R-output of the i-th picture element from this circuit 61. The same thing applies to Goi and Boi.)

In other words, the outputs are all monochrome.

When a calculation other than addition is performed between the wavelength components, in the blood flow analysis mode, the R-B mode, the R/G mode, etc., the selection of the coloring switch group 94 is not utilized, an image signal resulting in a monochrome image being output from the color adjustment/matrix/calculation circuit 61. The color processing circuit 65 processes the image signal resulting in a monochrome image and transforms it into an image signal resulting in a quasi-color image. In a mode in which calculations other than addition is performed between the wavelength region components, a monochrome image is obtained when the monochrome display switch 95 or the normal image switch 97 is selected, and a quasi-color image when the quasi-color switch 96 is selected.

In the calculation mode and the color selection mode, the color adjustment automatically becomes normal, the gains with respect to the R, G, B becoming normal. This is because the contents displayed are greatly influenced by the color adjustment, thereby disabling a quantitative and constant diagnosis to be performed, In the color selection mode, an image with the selected color is obtained when the normal image switch 97 is selected, and a monochrome image when the monochrome display switch 95 is selected. When the quasi-color switch 96 is selected, a quasi-color image is obtained.

In the calculation mode and the color selection mode, the selected mode and the constant are superimposed in the screen. When "G (1.7)" is displayed, it implies the G mode with $C_{11}=1.7$, and when "G+B (1.25/2)" is displayed, it implies the G+B mode with $C_6=1.25$ and $C_7=2$.

Next, the second calculation function, i.e., the R-G mode will be explained.

In this mode, the color adjustment is normal. Further, in this mode, a monochrome signal which can be expressed as $$Yoi = C_3 (Rii + C_4 \times Gii)$$

where $C_3$ and $C_4$ are constants. Generally, the value of $C_4$ is 2 to 4 and that of $C_5$ ca. 5. $C_3$ and $C_4$ can be set and changed at the keyboard 27. The operation method and the flashing and lighting of the LED 75 of the R-B output switch 122 are the same as in the case of the blood flow analysis switch 121. The switches 121 to 123, 114, 115 and the G+B switch 125, the R B switch 126, the R switch 127, the G switch 128 and the B switch 129 of the color selection switch group 92 compose a group of 10 selection switches from which one is to be selected, and by pressing one of the switches 121 to 123, 125 to 129, the contents of the fourth switch 54 are set. On the other hand, the switches 114 and 115 have the same functions, returning to the normal condition.

In this mode, the influence of the brightness due to surface reflection is removed, so that what is exclusively close to the condition in the celom wall depth can be visualized.

For $C_3$ and $C_4$, appropriate values are to be determined according to the disease and the region of interest.

The third calculation function, i.e., the R/G mode will now be described.

In this mode, the color adjustment is normal. Further, it is possible in this mode to visualize the change in the hue of the celom walls in an emphasized form. As to $C_5$ and $C_{13}$, appropriate values are to be set according to the principal disease in question and the region of interest to be examined.

Next, the color selection function will be described.

The color adjustment is normal in this case. The G+B mode mainly picks up any change in brightness. Unlike the G mode which is to be described later, it is effective for endoscopic examinations using different shades of blue.

In the R+G mode, the influence of the brightness of the non-pigment elements is removed in an endoscopic examination using different shades of brown or blue or a mixture of both, picking up any change in brightness due to the pigment examination itself. Since $C_9$ is provided here, the most appropriate display can be realized according to the pigment used.

In the R mode, the R component enables sub-mucosal or sub-epithelial blood vessels to be more clearly depicted, so that any sub-mucosal or sub-epithelial variation due to some disease can be observed together with the nature thereof.

In the G mode, the change in brightness enables micro-reddenings as well as the pattern and fine irregularities thereof to be perceived in the diagnosis of microcancers.

In the B mode, these irregularities can be perceived more clearly. The ON/OFF switching of the eight functions of the switches 121 to 123 and 125 to 129 is effected by the fourth switch 54. When any of the switches 121 to 123 and 125 to 129 is pressed at the operation panel 72, the LED of the switch pressed begins to flash. When the third switch 54 is pressed once, the mode becomes the one which has been set, and when the switch is pressed again, the normal condition, i.e. the condition in which Roi=Rii, Goi=Gii and Boi=Bii (However, the color adjustment is returned to the condition before the calculation mode and the color selection mode).

Next, the quasi-color function will be explained.

The switches 95 to 97 of the coloring switch group 94 compose a group of three switches from which one is to be selected. When the monochrome display switch 95 or the normal image switch 97 is selected while the calculation function and the color selection function are in operation, the color processing circuit 65 performs no operation at all, outputting the input signal as it is. When the quasi-color switch 96 is selected, the quasi-coloring processing according to the luminance of the input signal is performed.

In the normal condition (the condition corresponding to the normal output switch 91 or 93), the color processing circuit 65 performs nothing, irrespective of the positions of the switches 95 to 97. However, when the monochrome display switch 95 is set, the color adjustment/matrix/calculation circuit 61 performs the calculation shown in Tables 1.1 and 1.2, with the result that when the quasi-color switch 96 or the normal image switch 97 is selected, a normal color image is displayed and when the monochrome display switch 95 is selected, a monochrome image is selected. Tables 1.1 and 1.2 show the RGB-output signals from the color adjustment/matrix/calculation circuit 61. Here, the set values of $C_1$ to $C_{13}$ are input through the keyboard 27 according to the kind of the principal disease concerned and the region of interest to be examined.

TABLE 1.1

| Set mode | Set mode | | |
|---|---|---|---|
| | NORMAL | B/W | COLORING |
| Blood flow analysis mode (HEMO) | $Roi = 0.3\ C_1 \log_2 (Rii + C_2)/Gii + C_2)$<br>$Goi = 0.59\ C_1 \log_2 (Rii + C_2)/Gii + C_2)$<br>$Boi = 0.11\ C_1 \log_2 (Rii + C_2)/Gii + C_2)$ | $Roi = 0.3\ C_1 \log_2 (Rii + C_2)/Gii + C_2)$<br>$Goi = 0.59\ C_1 \log_2 (Rii + C_2)/Gii + C_2)$<br>$Boi = 0.11\ C_1 \log_2 (Rii + C_2)/Gii + C_2)$ | $Roi = 0.3\ C_1 \log_2 (Rii + C_2)/Gii + C_2)$<br>$Goi = 0.59\ C_1 \log_2 (Rii + C_2)/Gii + C_2)$<br>$Boi = 0.11\ C_1 \log_2 (Rii + C_2)/Gii + C_2)$ |
| R-B mode | $Roi = 0.3\ C_3 (Rii - C_4 Bii)$<br>$Goi = 0.59\ C_3 (Rii - C_4 Bii)$<br>$Boi = 0.11\ C_3 (Rii - C_4 Bii)$ | $Roi = 0.3\ C_3 (Rii - C_4 Bii)$<br>$Goi = 0.59\ C_3 (Rii - C_4 Bii)$<br>$Boi = 0.11\ C_3 (Rii - C_4 Bii)$ | $Roi = 0.3\ C_3 (Rii - C_4 Bii)$<br>$Goi = 0.59\ C_3 (Rii - C_4 Bii)$<br>$Boi = 0.11\ C_3 (Rii - C_4 Bii)$ |
| R/G mode | $Roi = 0.3\ C_5 (Rii/Gii + C_{13})$<br>$Goi = 0.59\ C_5 (Rii/Gii + C_{13})$<br>$Boi = 0.11\ C_5 (Rii/Gii + C_{13})$ | $Roi = 0.3\ C_5 (Rii/Gii + C_{13})$<br>$Goi = 0.59\ C_5 (Rii/Gii + C_{13})$<br>$Goi = 0.59\ C_5 (Rii/Gii + C_{13})$ | $Roi = 0.3\ C_5 (Rii/Gii + C_{13})$<br>$Goi = 0.59\ C_5 (Rii/Gii + C_{13})$<br>$Goi = 0.59\ C_5 (Rii/Gii + C_{13})$ |

TABLE 1.2

| Set mode | Set mode | | |
|---|---|---|---|
| | NORMAL | B/W | COLORING |
| G + B mode | $Roi = 0$<br>$Goi = Gii$<br>$Boi = Bii$ | $Roi = 0.3\ C_6 (Gii + C_7 Bii)$<br>$Goi = 0.59\ C_6 (Gii + C_7 Bii)$<br>$Boi = 0.11\ C_6 (Gii + C_7 Bii)$ | $Roi = 0.3\ C_6 (Gii + C_7 Bii)$<br>$Goi = 0.59\ C_6 (Gii + C_7 Bii)$<br>$Boi = 0.11\ C_6 (Gii + C_7 Bii)$ |
| R + B mode | $Roi = Rii$<br>$Goi = 0$<br>$Boi = Bii$ | $Roi = 0.3\ C_8 (Gii + C_9 Bii)$<br>$Goi = 0.59\ C_8 (Gii + C_9 Bii)$<br>$Boi = 0.11\ C_8 (Gii + C_9 Bii)$ | $Roi = 0.3\ C_8 (Gii + C_9 Bii)$<br>$Goi = 0.59\ C_8 (Gii + C_9 Bii)$<br>$Boi = 0.11\ C_8 (Gii + C_9 Bii)$ |
| R mode | $Roi = Rii$<br>$Goi = 0$<br>$Boi = 0$ | $Roi = 0.3\ C_{10} Rii$<br>$Goi = 0.59\ C_{10} Rii$<br>$Boi = 0.11\ C_{10} Rii$ | $Roi = 0.3\ C_{10} Rii$<br>$Goi = 0.59\ C_{10} Rii$<br>$Boi = 0.11\ C_{10} Rii$ |
| G mode | $Roi = 0$<br>$Goi = Gii$<br>$Boi = 0$ | $Roi = 0.3\ C_{11} Gii$<br>$Goi = 0.59\ C_{11} Gii$<br>$Boi = 0.11\ C_{11} Gii$ | $Roi = 0.3\ C_{11} Gii$<br>$Goi = 0.59\ C_{11} Gii$<br>$Boi = 0.11\ C_{11} Gii$ |
| B mode | $Roi = 0$<br>$Goi = 0$<br>$Boi = Bii$ | $Roi = 0.3\ C_{12} Bii$<br>$Goi = 0.59\ C_{12} Bii$<br>$Boi = 0.11\ C_{12} Bii$ | $Roi = 0.3\ C_{12} Bii$<br>$Goi = 0.59\ C_{12} Bii$<br>$Boi = 0.11\ C_{12} Bii$ |
| Normal mode | $Roi = Rii$<br>$Goi = Gii$<br>$Boi = Bii$ | $Roi = 0.3(0.3\ Rii + 0.59\ Gii + 0.11\ Bii)$<br>$Goi = 0.59(0.3\ Rii + 0.59\ Gii + 0.11\ Bii)$<br>$Boi = 0.11(0.3\ Rii + 0.59\ Gii + 0.11\ Bii)$ | $Roi = Rii$<br>$Goi = Gii$<br>$Boi = Bii$ |

When using the calculation function or the color selection function in combination with the quasi-color function, the quasi-color switch 96 may be set previously. By operating in this condition the fourth switch 54, a normal color image and an image which has undergone the processings of calculation and color selection as well as the quasi-color processing, can be alternately output and compared with each other.

Next, the contrast transformation function will be explained.

The contrast switch group 130 on the operation panel 72 includes five types (A to E) of contrast emphasis switches 131 to 135, a normal switch 136 and a gamma correction release switch 137. The built-in CRTs of the monitors 25 and 26 present no linear relationship between the input luminance signal and light emission. Consequently, it is necessary to establish a linear relationship between the output signal from the CCD 42 and the light emission in the monitors 25 and 26. Accordingly, when the normal switch 136 is selected, gamma correction of gamma=0.45 is performed in the contrast transformation circuit 62.

On the other hand, in the diagnosis of microcancers, a subtle change in brightness is an important diagnostic index. Accordingly, a function of emphasizing changes in brightness by intensifying contrast has been provided. Five contrast characteristics shown in FIGS. 4 to 8 have been provided. From these five types of characteristics, one is to be selected.

Figure 4:
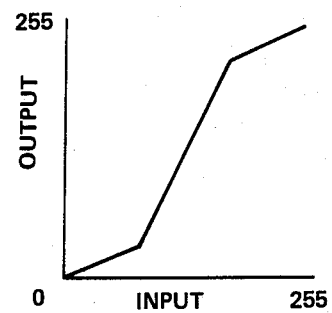
FIGS. 4 to 8 are characteristic diagrams showing the input/output characteristics of the contrast transformation circuit with respect to five different types of contrast intensifying switches selected.
Figure 6:
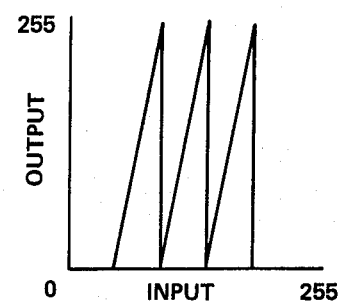
Figure 5:
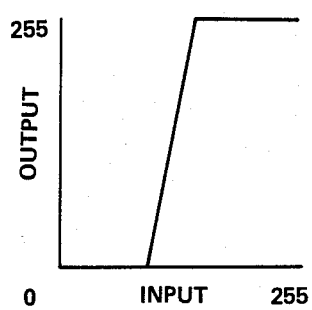
Figure 7:
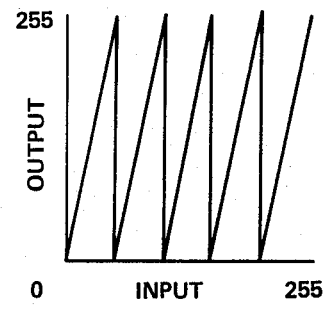
Figure 8:
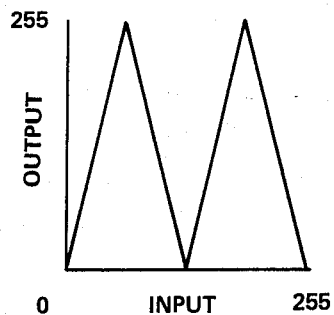

FIG. 4 shows a linear input/output characteristic graph with an enlarged intermediate linear section. FIG. 5 shows a characteristic in which no output is made for an input below a threshold, a linear output being effected for a narrow input range beyond this threshold. FIG. 6 shows a many-valued function characteristic giving a linear output for input signals beyond a threshold. FIG. 7 shows a many-valued function characteristic with no threshold. FIG. 8 shows a many-valued function characteristic with linear increase and decrease functions.

The above contrast emphasis switches 131 to 135, the normal switch 136 and the gamma correction release switch 137 compose a group of seven switches from which one is to be selected. By pressing any of the contrast emphasis switches 131 to 135, the LED thereof flashes. When in this condition the fifth switch 55 provided in the operation section is pressed, the LED 75 comes on and a contrast transformation of the characteristic corresponding to each of the switches 131 to 135 (FIGS. 4 to 8) is effected. When the fifth switch 55 is pressed again, the LED which has been ON returns to the flashing condition, the contrast characteristic being restored to the normal one. When the normal switch 136 is pressed, the contrast is restored to the normal condition, the contrast emphasis switches 131 to 135 and the gamma correction release switch 137 going out. When the output is being made with the normal contrast, the LED 75 of the normal switch 136 is always ON. Otherwise, the LED 75 of this switch 136 goes out.

Here, the normal contrast characteric implies the condition in which gamma is 0.45 (gamma for the entire system including the monitors 25 and 26 is 1).

The contrast transformation circuit 62 has an 8-bit memory capacity and transforms the ouptut relationship with respect to the input signals of 256 steps.

When the contrast emphasis switch 131 of A-type is selected, a characteristic as shown in FIG. 4 is obtained. In other words, the contrast in the intermediate ⅜ input signal range is double the normal one. The contrast deteriorates for dark and bright portions. In this A-type, the contrast of regions which are important for diagnosis (portions with intermediary brightness) can be emphasized without extremely changing the way the brightness and the hue are perceived.

When the contrast emphasis switch 132 of B-type is selected, the characteristic is the one shown in FIG. 5. The contrast in the intermediary area is five times as intensive as the normal one. This B-type is used in exclusively aiming at and empahsizing any change in brightness. The latitude that is actually selected is extremely narrow, so that it is possible to successively change brightness using the brightness switch group 113 or the third switch 53, in particular, the latter, and fix any desirable display by manipulating the third switch 53.

The characteristic corresponding to the contrast emphasis switch 133 of C-type is the one shown in FIG. 6. The latitude is enlarged when compared with the one in FIG. 5. The darkest and brightest portions are displayed in black, so that a neat display can be obtained, the diagnostically unnecessary portions such as the brightest ones being deleted.

When the contrast emphasis switch 134 of D-type is selected, the characteristic obtained is the one shown in FIG. 7. The contrast is emphasized without affecting the original latitude.

Selection of the contrast emphasis switch 135 of E-type results in the characteristic shown in FIG. 8.

Here, when the degree of contrast emphasis desired is such that the appearance is not extremely changed, the emphasis magnification should not be beyond the range of 1.5 to 2.5. When combined with the outline emphasis, the difference in brightness is more easier to discriminate. When an extreme change in apperance is desired, an emphasis magnification of four or more may be effective. In this case, a more effective emphasis can also be effected in combination with the outline emphasis and the quasi-coloring. Since the outline emphasis circuit 63 is arranged after the contrast transformation circuit 62, the outline emphasis amount (pre-shoot amount, overshoot amount) itself is not further enlarged, thus providing a natural appearance.

The gamma correction release switch 137 serves to disable the gamma correction function to be effective. It is used when the output of the CCD 42 is not output, avoinding its processing as far as possible. In other words, when the gamma correction release switch 137 is set and the fifth switch 55 is pressed, the function of the contrast trasnformation circuit 62 is stopped, an output signal proportionate to the output signal of the CCD 42 being output from the video processor 24 (gamma =1).

The outline emphasis function will now be explained.

The outline emphasis switch group 140 includes three outline emphasis switches 141 to 143 of different intensities as well as a release switch 144.

The above switches compose a group of four switches from which one is to be selected. The LED of any of these switches selected comes on, those of the others going out. When the outline emphasis switch 143 of a normal emphasis degree is selected, an ordinary outline emphasis is effected for all the R, G, B signals, without depending on the selection of the coloring switch group 94.

When the outline emphasis switch 142 of an intensitive (high) level is selected, an outline emphasis of an intensity higher than the ordinary one is effected for all the R, G, B signals, without depending on the setting of the coloring switch group 94.

When the outline emphasis switch of a special intensity 141 is selected, the setting of the coloring switch group 94 is not utilized, and when an ordinary image is output using the video processor 24, an outline emphasis which is more intensitive than the usual one is effected for R and B; for G, an outline emphasis which is still more intensitive than the one corresponding to the intensitive level switch 142 is performed. When the apparatus is used as a video processor for outputting monochrome or quasi-colored images, the same outline emphasis as the one corresponding to the intensitive level outline emphasis switch 142. Since the human visual sensitivity is acute to G, the outline emphasis with respect to G is highly effective. On the other hand, the outline emphasis with respect to R and B are relatively ineffective, so that over-performing thereof will only result in the noises being conspicuous.

Accordingly, the degree of emphasis with respect to R and B has not been hightened very much, only G being intensively emphasized, thereby attaining a maximum emphasis, with noises restrained to a minimum. With respect to G only, the selection is not performed in two step but in three: normal, intensive, extra-intensive, so that an elaborate selection according to the cases can be performed. When the outline emphasis switch 144 is selected, the selection of the coloring switch group 94 is not utilized. No outline emphasis is then effected at all, a signal which has been processed as little as possible being output.

The external control function will now be described.

When an external control switch 151 on the operation panel 72 is pressed, the external control mode becomes ON, the LED 75 of this switch 151 coming on. When this switch 151 is pressed again, the LED of this switch 151 goes out, the previous condition being restored. In the external control mode, various image processings are performed such as the calculation processing, the contrast emphasis processing, the coloring processing, the extraction of the spectral transmission characteristics of the rotary filter 38 and of the specific wavelength components which are not related to the image (the wavelength can be fixed on the basis of the RGB intensity ratio on the R, G, B frame memories 48R, 48G, 48B, so that it is possible, for example, to exclusively extract the wavelength region of 600 nm to 622 nm.

The contents of the image processing are stored in the floppy disk beforehand so as to be read out at the FDD 31. In other words, the operator can perform the processing with arbitrarily selected characteristics. The writing to the floppy disk is performed by a computer which is not shown and the FDD.

Since the video processor 24 of this embodiment is equipped with a very large number of functions, the operator may, in some cases, be confused in the operation thereof, resulting in a hindered endoscopic examination. Accordingly, a normal line 112 is provided on the operation panel 72, the normal (or reference) conditions being arranged in a line, so that any confusion can be easily restored to the normal or reference condition.

Further, an all clear switch 152 is provided on the operation panel 72. When this switch 152 is pressed, all the functions are restored to the normal or reference conditions (all the switches are set on the normal line 112), an arrangement which is very convenient.

Figure 9:
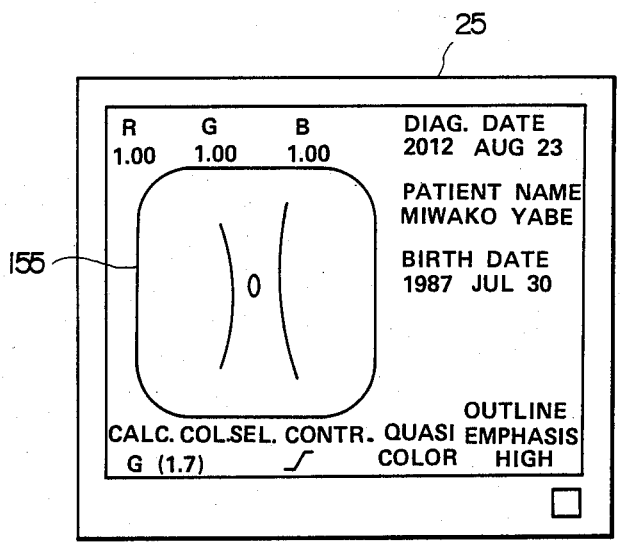
FIG. 9 is a schematic view illustrating how the data and the setting conditions of various functions are superimposed on the monitor screen.

The superimpose circuit 68 displays the data and the setting conditions of various functions on the monitor screen in a state superimosed on an endoscopic image 155, as shown in FIG. 9. Here, R1.00, G1.00 and B1.00 respectively show to how many times more intensive values the gains of color adjustment are set. In the screen shown, the color selection is set to G, which is quasi-color displayed, so that the R, G, B gains all automatically return to the reference value, which is 1.00 for all of them. When the fourth switch 54 is pressed, a normal color image is restored, the then R, G, B gains returning to the original values. They are displayed, for example, as R0.8, G1.02, B0.97.

Here, the color adjustment/matrix/calculation circuit 61, the contrast transformation circuit 62, the outline emphasis circuit 63 and the color processing circuit 65 are digital image processing circuits each having a frame memory. As to the processing flow in each of them, a well-known technique may be employed, so that the description thereof will be omitted here. Further, the frame memories 48R, 48G, 48B and the circuits shown at 61 to 65 may be regarded as a single digital image processing circuit so as to simplify the configuration of the circuit and program by reducing the number of frame memories.

Further, an analog image processing may be performed intead of the digital one. In particular, with respect to the outline emphasis etc., adopting an analog processing will result in a smaller circuit.

The present invention can be applied not only to the surface-sequential-type endoscope (endoscopic system) but also to a system composed of an electronic scope witn a built-in color filter used under a white light illumination. It is also applicable to a case where images are picked up by a TV camera mounted on the eyepiece section of a fiber scope.

Since the above color adjustment/matrix/calculation circuit 61 is arranged before the contrast transformation circuit 62, the outline emphasis circuit 63 or the like, an accurate operation is to be expected. The color adjustment/matrix/calculation circuit 61 is arranged before the position where the gamma correction is genrally performed (in this embodiment, it is perfomred in the contrast transformation circuit 62), so that an accurate output is also to be expected in this connection. It is natural that this color adjustment/matrix/calculation circuit 61 should be placed before the color processing circuit 65.

The outline emphasis circuit may be placed after the color processing circuit 65.

Since the color adjustment/matrix/calculation circuit 61 is placed after the contrast transformation circuit 62 and the outline emphasis circuit 63, an image with a proper brightness can be obtained even when various processings are performed. The light intensity adjustment circuit 64 may be placed after the color processing circuit 65. It is also possible to digital-output image signals without performing D/A conversion. Further, the superimpose circuit 68 may be a digital circuit which is placed before the D/A converter 67.

As for the VTR 28, SVF 29 and AUX 30, they can be commercially available products for normal NTSC.

Besides the keyboard 27, data on patients may be input by means of a magnetic card, an IC card or an optical card.

Further, instead of MTSC, PAL or SECAM may be employed. In the case of monochrome display, the color temperature may be high or low. A little difference in hue may be admitted. In other words, various modifications may be possible in the range providing the same effect.

Figure 10:
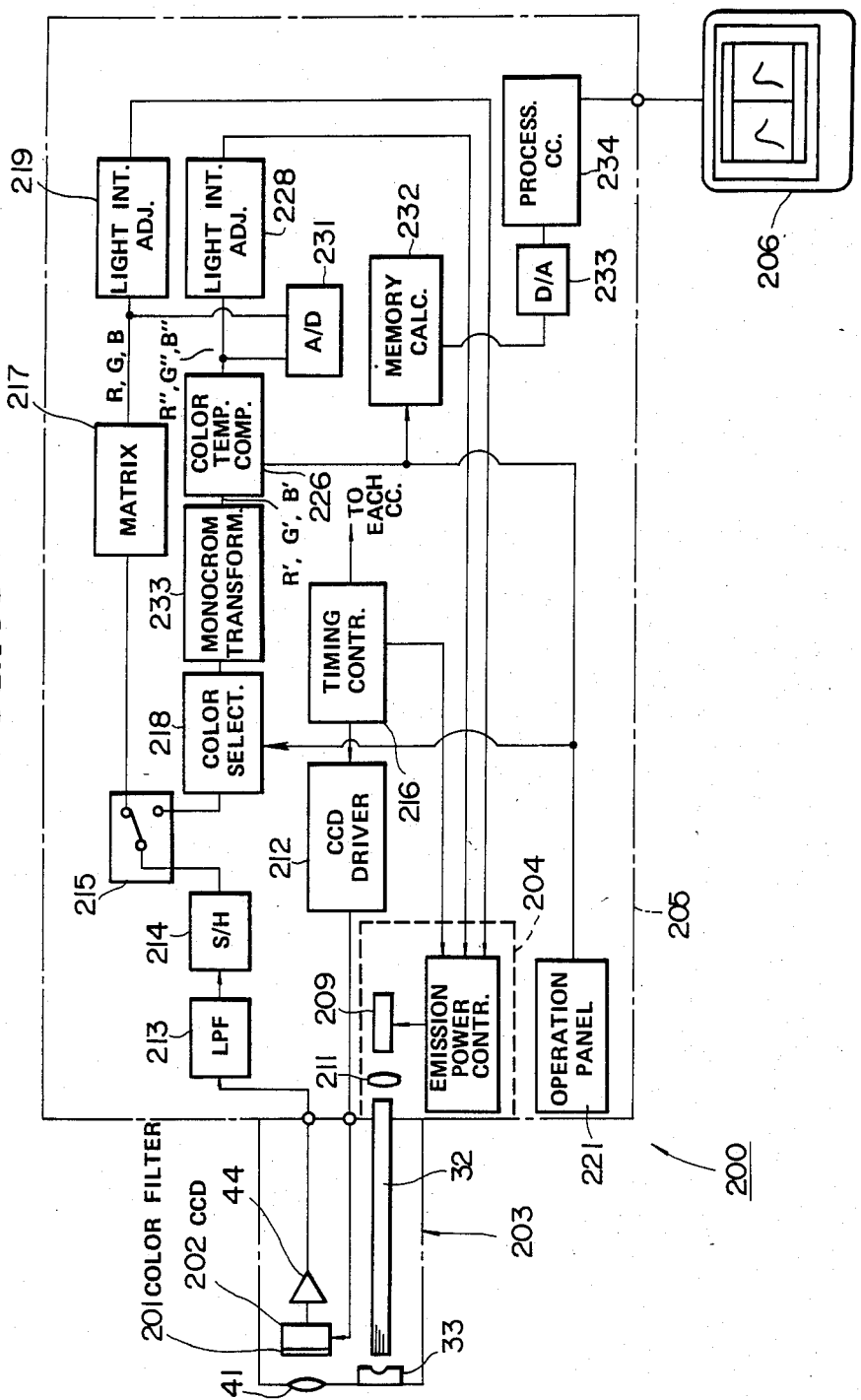
FIG. 10 is a block diagram showing the configuratin of the third embodiment of an endoscope apparatus in accordance with this invention.
Figure 13:
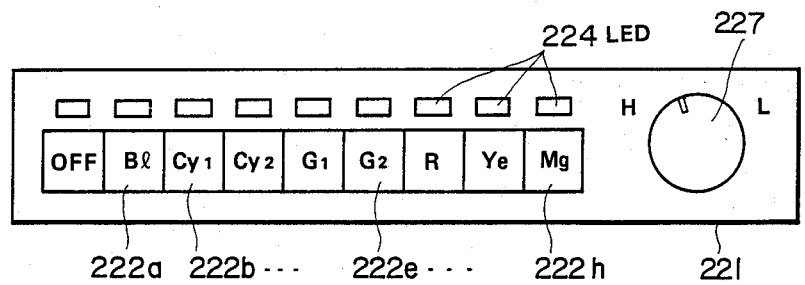
FIG. 13 a front view showing the operation panel portion where the selection switches for selecting images obtained by specific filters are provided.

FIG. 10 shows an endoscope apparatus 200 which is the third embodiment of this invention.

This endoscope apparatus 200 is composed of: an electronic scope 203 using a CCD 202 on which a color filter 201 is mounted; a video processor 205 including a light source section 204 adapted to supply illuminating light to the electronic scope 203 and a signal processing system; and a monitor 206 adapted to display image signals output through output terminals of this video processor 205.

The above CCD 202 has 584 (longitudinal) × 390 (lateral) picturee elements, the image pickup section thereof being a regular square. The color filter 201 is mounted on the front surface of the image pickup section of this CCD 202, effecting color separation for each picture element. As shown in FIG. 11, the color filter 201 is composed of a multitude of units each consisting of filter units for eight picture elements, i.e., four filters $Mg$, $Cy_1$, $B1$, $Cy_2$ arranged in the first row and another four filters $G_1$, $Ye$, $G_2$, $R$ arranged in the second row.

FIGS. 12A and 12B show the spectral transmission characteristics of the above eight filters $Mg$, $Cy_1$, ..., $R$.

As to the other components of the above electronic scope 203, they have already been described with reference to FIG. 2, so that the description thereof will be omitted here.

The above light source section 204 depends on the drive power supplied by an emission control circuit 208 and the illuminating light of a flashing strobolamp 209 is condensed by a condenser lens 211 and supplied to the incidence end surface of the light guide 32.

The signals read out of a CCD drive 202 by the application of the drive signals from a CCD drive 212 are amplified by the amplifier 44 and input to a selector 215 through a low-pass filter 213 and a sample/hold circuit 214. The CCD 202 is driven at a rate of 60 fields and 60 frames per second.

The above selector 215 is switched over for each frame by a timing control circuit 216 adapted to perform timing control of each circuit and transmits the output of the sample/hold circuit 214 to a matrix circuit 217 or a color selelction circuit 218.

The above matrix circuit 217 exclusively uses those outputs of the CCD which have past through the filters $Mg$, $G_1$, $Cy_1$, and $Ye$ and performs normal color calculation so as to convert them into R, G, B signals and output them to a light intensity adjustment corcuit 219. This light intensisty adjustment circuit 219 generates light intensity adjustment signals out of the R, G, B signals and output them to the emission control circuit 208 so as to adjust the light emission of the strobolamp 209.

On the other hand, the color selection circuit 218 serves to exclusively select the picture element outputs corresponding to specific filters by means of selection switches $222a$, ..., $222h$ provided on an operation panel 221 and output them to the monochrome transformation circuit 223. For example, when the selection switch $222e$ is selected, the output of only those picture elements which have past through the filter $G_2$ is output to the mochrome transformation circuit 223. When any of the selection switches $222a$, ..., $222h$ is selected, an LED 224 arranged above that switch comes on.

The above monochrome transformation circuit 223 serves to evenly divide the input signals into three parts, which are multiplied by 3, 5.9 and 1.1, respectively, and output to a color temperature correction circuit 226 as signals R', G', B' corresponding to the signals R, G, B.

This color temperature correction circuit 226 is adapted to transform (change) color temperature by a command on the basis of a color temperature adjustment knob 227. If this color temperature correction circuit 226 is not provided, the output signals of the monochrome transformation circuit 218 are displayed on a monitor 205 as white. When, on the other hand, such a color temperature corection circuit 226 is provided, the color temperature of the white when displayed on the monitor 205 can be adjusted by properly increasing or decreasing the levels of the input signals R', G', B'

The output signals of the above color temperature correction circuit 226 generate, after passing a light intensity adjustment circuit 228, light intensity adjustment signals, which are input to the light emission control circuit 208.

Figure 14:
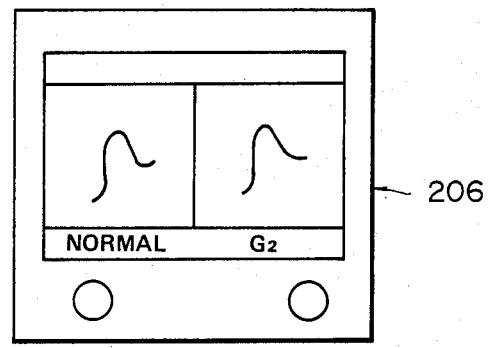
FIG. 14 is a schematic view illustrating how an image with respect to a specific wavelength region obtained by a filter selected is displayed on the monitor together with a normal color image.

The output signals R", G", B" of the above color temperature correction circuit 226 are input to an A/D converter 231, along with the output signals R, G, B of the matrix circuit 217, and after being transformed into digital signals, they are input to a memory calculation circuit 232 so as to perform synchronization of the output signals. This synchronization is performed to convert the display positions when two images on the basis of the R, G, B signals output from the matrix circuit 217 and the R", G", B" signals output from the color temperature correction circuit 226 are displayed, as shown in FIG. 14, side by side on a single monitor 206. At the same time, the circuit performs the calculation of line interpolation so as to attain uniformity in size. Further, it outputs characters such as "NORMAL" and "$G_2$", thereby making it possible to discriminate whether the displayed image is a normal one or one which has passed through the filter $G_2$.

The signals which have passed through the above memory calculation circuit 232 are converted into analog signals by a D/A converter 233. After that, they are transformed into image signals of a predetermined system by a processing circuit 234 and displayed on the monitor 206.

The strobolamp 209 in the light source section 204 perfomrs light emission by the light intensity adjustment signals from the light intensity adjustment circuits 219 and 228, in such a manner that an appropriate emission is alternately effected for each of the frames in CCD 202 so that an appropriate light amount may be obtained for both the normal color image and the specific wavelength region image.

This embodiment is based on the NTSC system in that the image signals thereof are of 525 scanning lines, 60 fields and 30 frames, an interlace display being effected.

The above CCD 202 alternately picks up images for the normal color image and the specific wavelength region image with an appropriate brightness for both of them. This is performed at a rate of 30 times per second and is repeated 60 times. Here, the CCD 202 has 584 longitudinal picture elements and four picture elements in the longitudinal direction compose one set corresponding to one scanning line. In Field A of the NTSC, they are displayed at an interval of one scanning line. In Field B, a line interpolation output with the contents of Field A is displayed. Accordingly, the size of the display screen of the monitor 206 may be that of a regular square with 292 scanning lines, and, as shown in FIG. 14, a normal color image and a specific wavelength region image are simultaneously displayed, side by side.

Since in this embodiment the normal color image and the specific wavelength region image are thus simultanously displayed, the physician is enabled to perform a sophisticated diagnosis by comparing the two images with each other.

Furthermore, the normal color image and the specific wavelength region image present an appropriate brightness, in particular, irrespective of the wavelength region selected. Besides, the quantity of light for illumination is different for the normal color image and the specific wavelength region image, so that an image with a satisfactory S/N can always be obtained.

Further, since the light emission is effected by the strobolamp 209, the intensity in the quantity of light can be arbitrarily changed for each frame. A rapid adjustment of the quantity of light would be difficutlt to realize with a diaphragm.

Furthermore, since the color temperature correction circuit 226 is provided so as to enable the color temperature of a monochrome image to be varied, adjustment can be conducted according to the illumination color inside the endscope as well as the taste of the operator, so that a color temperature that is most comfortable to the eye can be selected. As for the circuits composing the system, they can be prepared in accordance with a well-known art.

What is claimed is:

1. An endoscope apparatus, comprising:
   an optical endoscope composed of:
   an elongate inserting section,
   a light guide inserted into said inserting section and adapted to transmit a light beam applied to an incidence end surface and give it off through an outlet end surface,
   an objective optical system adapted to form the image of a subject illuminated, and
   an image guide adapted to transmit the image obtained by said objective optical system to the side of an eyepiece;
   a television camera composed of:
   a lens adapted to form the image transmitted by said image guide, and
   a solid image pickup element arranged at the position where the image forming is effected by said lens and equipped with a photoelectric transformation function;
   a light source means adapted to supply illuminating light to the incidence end surface of said light guide;
   an image signal processing means composed of:
   a color image signal generating means adapted to generate predetermined color image signals by performing signal-processing with respect to said solid image pickup element, and
   a specific-wavelength-region-image signal generating means equipped with output terminals adapted to emit image signals based exclusively on specific wavelength region components in the visible region for generating said color image signals; and
   a display means composed of:
   a color image display section adapted to display said color image signals, and
   a specific-wavelength-image-display section adapted to display said image signals based exclusively on specific wavelength region components.

2. An endoscope apparatus, comprising:
   an electronic endoscope composed of:
   an elongate inserting section,
   a light guide inserted into said inserting section and adapted to transmit a light beam applied to an incidence end surface and give it off through an outlet end surface,
   an objective optical system adapted to form the image of a subject illuminated, and
   a solid image pickup element arranged on the focal surface of said objective optical system and equipped with a photoelectric transformation function;
   a light source means adapted to supply illuminating light to the incidence end surface of said light guide;
   an image signal processing means composed of:
   a color image signal generating means adapted to generate predetermined color image signals by performing signal-processing with respect to said solid image pickup element, and
   a specific-wavelength-region-image signal generating means equipped with output terminals adapted to emit image signals based exclusively on specific wavelength region components in the visible region for generating said color image signals; and
   a display means composed of:
   a color image display section adapted to display said color image signals, and
   a specific-wavelength-image-display section adapted to display said image signals based exclusively on specific wavelength region components.

3. An apparatus as claimed in claim 1 or 2, wherein said light source means is composed of a lamp adapted to output white light and a condenser lens adapted to condense the light of said lamp and apply it to the incidence end surface of said light guide.

4. An apparatus as claimed in claim 1 or 2, wherein said light source means is composed of a lamp adapted to output white light, a rotary filter equipped with color transmission filters covering as a whole the visible wavelength region, each passing exclusively the light of a specific wavelength which is different for different filters, a motor adapted to rotate said rotary filter, and a condenser lens adapted to condense the light transmitted through the color transmission filter placed in the optical path of said rotary filter and apply it to the incidence end surface of said light guide.

5. An apparatus as claimed in claim 4 further comprising a diaphragm for varying the quantity of light applied to said light guide.

6. An apparatus as claimed in claim 1 or 2, wherein said color image signal generating means generates three primary color signals of the NTSC system.

7. An apparatus as claimed in claim 1 or 2, wherein said color image signal generating means generates composite image signals of the NTSC system.

8. An apparatus as claimed in claim 1 or 2, wherein said specific-wavelength-region-image signal generating means outputs three primary color signals by performing an inverse matrix processing of the color difference signals which are generated when the signal processing is effected by said color image signal generating means.

9. An apparatus as claimed in claim 4, wherein said specific-wavelength-image signal generating means outputs signals read out by said solid image pickup means under the illuminating light which has passed through said color transmission filters.

10. An apparatus as claimed in claim 4, wherein said image signal processing means has memories adapted to temporarily store images.

11. An apparatus as claimed in claim 10, wherein said electronic endoscope has switches for freeze operation.

12. An apparatus as claimed in claim 7, further comprising a video tape recorder and a still video floppy device adapted to record said composite image signals.

13. An apparatus as claimed in claim 1 or 2, wherein said image signal processing means has a tone varying means adapted to vary the gain with respect to the color signals.

14. An apparatus as claimed in claim 5, wherein said image signal generating means has a means for generating light-intensity-adjustment signals which are adapted to control the aperture of said diaphragm accoridng to the output signal level of said solid image pickup element.

15. An apparatus as claimed in claim 1 or 2, wherein said image signal processing means has a means for adjusting the output level of the specific-wavelength-region-image signals output through said output terminals.

16. An apparatus as claimed in claim 1 or 2, wherein said image signal processing means has a contrast transformation means whose input/output characteristic is not linear.

17. An apparatus as claimed in claim 1 or 2, wherein said image signal processing means has a calculating means adapted to perform the calculation of adding a constant to the red color signal and dividing the sum by the sum of the green color signal and a constant, the quotient being logarithmically processed for the purpose of blood flow analysis.

18. An apparatus as claimed in claim 1 or 2, wherein said image signal processing means has an outline emphasis means.

19. An apparatus as claimed in claim 3, wherein said lamp is a strobolamp which is capable of flash light emission.

20. An apparatus as claimed in claim 1 or 2, wherein a mosaic color filter is attached to the image pickup surface of said solid image pickup element for the purpose of color separation, said mosaic color filter consisting of a plurality of color transmission filters of different transmission regions arranged in a mosaic fashion.

21. An apparatus as claimed in claim 20, wherein said mosaic color filter is composed of a multitude of filter units arranged crosswise, each filter unit consisting of eight color transmission filters respectively passing the wavelength regions of magenta, cyan, blue, narrow-band cyan, green, yellow, narrow-band green, and red.

22. An apparatus as claimed in claim 21, wherein said color image signal generating means generate color image signals out of the output of the picuture elements which have passed through four of said color transmission filters, magenta, cyan, green, and yellow.

23. An apparatus as claimed in claim 20 or 21, further comprising a selection switch adapted to exclusively display an image which has passed through one of said plurality of color transmission filters.

24. An apparatus as claimed in claim 1 or 2, wherein said image signal processing means includes an image signal transformation means adapted to transform said color image signals and said specific-wavelength-region-image signals into image signals in accordance with a predetermined standard.

25. An apparatus as claimed in claim 24, wherein said display means is so designed that said color image display section and said specific-wavelength-region-image display section are displayed on the same monitor screen.

26. An apparatus as claimed in claim 1 or 2, wherein said display means is so designed that said color image display section and said specific-wavelength-image display section are displayed on separate monitors.

* * * * *